United States Patent
Zhou et al.

(10) Patent No.: US 9,670,474 B2
(45) Date of Patent: *Jun. 6, 2017

(54) FUSED NHASE WITH IMPROVED SPECIFIC ACTIVITY AND STABILITY

(71) Applicants: Zhemin Zhou, Wuxi (CN); Wenjing Cui, Wuxi (CN); Zhongmei Liu, Wuxi (CN); Li Zhou, Wuxi (CN); Yuanyuan Xia, Wuxi (CN)

(72) Inventors: Zhemin Zhou, Wuxi (CN); Wenjing Cui, Wuxi (CN); Zhongmei Liu, Wuxi (CN); Li Zhou, Wuxi (CN); Yuanyuan Xia, Wuxi (CN)

(73) Assignee: Jiangnan University, Wuxi, Jiangsu (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/870,023

(22) Filed: Sep. 30, 2015

(65) Prior Publication Data

US 2016/0312206 A1 Oct. 27, 2016

(30) Foreign Application Priority Data

Apr. 22, 2015 (CN) .......................... 2015 1 0195795

(51) Int. Cl.
  *C12N 9/88* (2006.01)
  *C12P 13/02* (2006.01)
(52) U.S. Cl.
  CPC ................ *C12N 9/88* (2013.01); *C12P 13/02* (2013.01); *C12Y 402/01084* (2013.01)

(58) Field of Classification Search
None
See application file for complete search history.

(56) References Cited

U.S. PATENT DOCUMENTS

2010/0047863 A1* 2/2010 Eck .......................... C12N 9/88
435/69.1

OTHER PUBLICATIONS

Foerstner et al., "A Nitrile Hydratase in the Eukaryote Monosiga brevicollis", PLoS One, Dec. 2008, 3(12):e3976. doi:10.1371/journal.pone.0003976.*
Xia et al., "Construction of a subunit-fusion nitrile hydratase and discovery of an innovative metal ion transfer pattern", Nature: Scientific Reports, 2016, 6:19183, pp. 1-13. DOI: 10.1038/srep19183.*
Sakashita et al., "Transcriptional Regulation of the Nitrile Hydratase Gene Cluster in Pseudomonas chlororaphis B23", Journal of Bacteriology, Jun. 2008, vol. 190, No. 12, 4210-4217. doi:10.1128/JB.00061-08.*

* cited by examiner

*Primary Examiner* — Suzanne M Noakes
(74) *Attorney, Agent, or Firm* — Lili Chen (57) ABSTRACT

The present invention provides a fused NHase with improved specific activity and stability, which relates to the field of genetic engineering. This invention provides a method of overexpressing a fused NHase in *E. coli* and producing a mutant NHase with improved the stability and product tolerance. The invention provides a simple, efficient and safe method of making mutant NHase, and can produce a large amount of soluble NHases in a short period. The present invention makes a contribution to large-scale industrial production and further theoretical study of NHases.

10 Claims, 4 Drawing Sheets

SEQUENCE LISTING

```
<160> NUMBER OF SEQ ID NOS: 20

<210> SEQ ID NO 1
<211> LENGTH: 1822
<212> TYPE: DNA
<213> ORGANISM: Artificial
<220> FEATURE:
<223> OTHER INFORMATION: Synthesized Sequence

<400> SEQUENCE: 1
```

```
ccacaccagg agaaccgcac catggggcaa tcacacacgc atgaccacca tcacgacggg      60
taccaggcac cgcccgaaga catcgcgctg cgggtcaagg ccttggagtc tctgctgatc     120
gagaaaggtc ttgtcgaccc agcggccatg gacttggtcg tccaaacgta tgaacacaag     180 gtaggcccccc gaaacggcgc caaagtcgtg gccaaggcct gggtggaccc tgcctacaag     240
gcccgtctgc tggcagacgc aactgcggca attgccgagc tgggcttctc cggggtacag     300
ggcgaggaca tggtcattct ggaaaacacc cccgccgtcc acaacgtctt cgtttgcacc     360
ttgtgctctt gctacccatg gccgacgctg gcttgcccc ctgcctggta caaggccgcc     420
gcctaccggt cccgcatggt gagcgacccg cgtggggttc tcgcggagtt cggcctggtg     480
atccccgcca acaaggaaat ccgcgtctgg gacaccacgg ccgaattgcg ctacatggtg     540
ctgccggaac ggcccggaac tgaagcctac agcgaagaac aactggccga actcgttacc     600
cgcgattcga tgatcggcac cggcctgcca acccaaccca ccccatctca ttaaggagtt     660
cgtcatgaat ggcattcacg atactggcgg agcacatggt tatgggccgg tttacagaga     720
accgaacgaa cccgtctttc gctacgactg gaaaaaacg gtcatgtccc tgctcccggc     780
cctgctcgcc aacgcgaact tcaacctcga tgaatttcgg cattcgatcg agcgaatggg     840
cccggcccac tatctggagg gaacctacta cgaacactgg cttcatgtct ttgagaacct     900
gctggtcgag aagggtgtgc tcacggccac ggaagtcgcg accggcaagg ctgcgtctgg     960
caagacggca acgcgcgtgc tgacgccggc catcgtggac gactcgtcag caccggggct    1020
tctgcgcccg ggaggagggt tctctttttt tcctgtgggg gacaaggttc gcgtcctcaa    1080
caagaacccg tgggccata cccgcatgcc gcgctacacg cgggcaaagt ggggacagtg    1140
gtcatcgacc atggtgtgtt tcgtgacgcc ggacaccgcg gcacacggaa agggcgagca    1200
gccccagcac gtttacaccg tgagtttcac gtcggtcgaa ctgtgggggc aagacgcttc    1260
ctcgccgaag gacacgattc gcgtcgactt gtgggatgac tacctggagc cagcgtgatc    1320
atgaaagaca aacggtttcc attgccagag ggttcgctga aggacctcga tggccctgtg    1380
tttgacgagc cttggcagtc ccaggcgttt gccttggtgg tcagcatgca caaggccggt    1440
ctctttcagt ggaaagactg ggccgagacc ttcaccgccg aaatcgacgc ttccccgctc    1500
tgccggcgaa agcgtcaacg acacctacta ccggcaatgg gtgtcggcgc tggaaaagtt    1560
ggtggcgtcg ctgggcttg tgacgggtgg agacgtcaac tcgcgcgcac aggagtggaa    1620
acaggcccac ctcaacaccc cacatgggca cccgatcctg ctggcccatg cgctttgccc    1680
gccagcgatc gaccccaagc acaagcacga gccacaacgc tcaccgatca aggtcgttgc    1740
cgcaatggct tgagatccac tgtcctgttt ccctaccttg aatggagtaa accatgtctt    1800
cattttctac cactgctgtc cc                                             1822
```

<210> SEQ ID NO 2
<211> LENGTH: 219
<212> TYPE: PRT
<213> ORGANISM: Artificial
<220> FEATURE:
<223> OTHER INFORMATION: Synthesized Sequence

<400> SEQUENCE: 2

```
Met Asn Gly Ile His Asp Thr Gly Gly Ala His Gly Tyr Gly Pro Val
1               5                   10                  15

Tyr Arg Glu Pro Asn Glu Pro Val Phe Arg Tyr Asp Trp Glu Lys Thr
            20                  25                  30

Val Met Ser Leu Leu Pro Ala Leu Leu Ala Asn Gly Asn Phe Asn Leu
```

```
            35                  40                  45
Asp Glu Phe Arg His Ser Ile Glu Arg Met Gly Pro Ala His Tyr Leu
     50                  55                  60

Glu Gly Thr Tyr Tyr Glu His Trp Leu His Val Phe Glu Asn Leu Leu
 65                  70                  75                  80

Val Glu Lys Gly Val Leu Thr Ala Thr Glu Val Ala Thr Gly Lys Ala
                 85                  90                  95

Ala Ser Gly Lys Thr Ala Thr Pro Val Leu Thr Pro Ala Ile Val Asp
                100                 105                 110

Gly Leu Leu Ser Thr Gly Ala Ser Ala Ala Arg Glu Glu Gly Ala Arg
            115                 120                 125

Ala Arg Phe Ala Val Gly Asp Lys Val Arg Val Leu Asn Lys Asn Pro
        130                 135                 140

Val Gly His Thr Arg Met Pro Arg Tyr Thr Arg Gly Lys Val Gly Thr
145                 150                 155                 160

Val Val Ile Asp His Gly Val Phe Val Thr Pro Asp Thr Ala Ala His
                165                 170                 175

Gly Lys Gly Glu His Pro Gln His Val Tyr Thr Val Ser Phe Thr Ser
            180                 185                 190

Val Glu Leu Trp Gly Gln Asp Ala Ser Ser Pro Lys Asp Thr Ile Arg
        195                 200                 205

Val Asp Leu Trp Asp Asp Tyr Leu Glu Pro Ala
    210                 215

<210> SEQ ID NO 3
<211> LENGTH: 211
<212> TYPE: PRT
<213> ORGANISM: Artificial
<220> FEATURE:
<223> OTHER INFORMATION: Synthesized Sequence

<400> SEQUENCE: 3

Met Gly Gln Ser His Thr His Asp His His Asp Gly Tyr Gln Ala
 1               5                  10                  15

Pro Pro Glu Asp Ile Ala Leu Arg Val Lys Ala Leu Glu Ser Leu Leu
                 20                  25                  30

Ile Glu Lys Gly Leu Val Asp Pro Ala Ala Met Asp Leu Val Val Gln
             35                  40                  45

Thr Tyr Glu His Lys Val Gly Pro Arg Asn Gly Ala Lys Val Val Ala
     50                  55                  60

Lys Ala Trp Val Asp Pro Ala Tyr Lys Ala Arg Leu Leu Ala Asp Gly
 65                  70                  75                  80

Thr Ala Gly Ile Ala Glu Leu Gly Phe Ser Gly Val Gln Gly Glu Asp
                 85                  90                  95

Met Val Ile Leu Glu Asn Thr Pro Ala Val His Asn Val Phe Val Cys
                100                 105                 110

Thr Leu Cys Ser Cys Tyr Pro Trp Pro Thr Leu Gly Leu Pro Pro Ala
            115                 120                 125

Trp Tyr Lys Ala Ala Pro Tyr Arg Ser Arg Met Val Ser Asp Pro Arg
        130                 135                 140

Gly Val Leu Ala Glu Phe Gly Leu Val Ile Pro Ala Asn Lys Glu Ile
145                 150                 155                 160

Arg Val Trp Asp Thr Thr Ala Glu Leu Arg Tyr Met Val Leu Pro Glu
                165                 170                 175

Arg Pro Ala Gly Thr Glu Ala Tyr Ser Glu Glu Gln Leu Ala Glu Leu
```

-continued

```
                     180                 185                 190
Val Thr Arg Asp Ser Met Ile Gly Thr Gly Leu Pro Thr Gln Pro Thr
                 195                 200                 205

Pro Ser His
        210

<210> SEQ ID NO 4
<211> LENGTH: 144
<212> TYPE: PRT
<213> ORGANISM: Artificial
<220> FEATURE:
<223> OTHER INFORMATION: Synthesized Sequence

<400> SEQUENCE: 4

Met Lys Asp Glu Arg Phe Pro Leu Pro Glu Gly Ser Leu Lys Asp Leu
1               5                   10                  15

Asp Gly Pro Val Phe Asp Glu Pro Trp Gln Ser Gln Ala Phe Ala Leu
            20                  25                  30

Val Val Ser Met His Lys Ala Gly Leu Phe Gln Trp Lys Asp Trp Ala
        35                  40                  45

Glu Thr Phe Thr Ala Glu Ile Asp Ala Ser Pro Ala Leu Pro Gly Glu
    50                  55                  60

Ser Val Asn Asp Thr Tyr Tyr Arg Gln Trp Val Ser Ala Leu Glu Lys
65                  70                  75                  80

Leu Val Ala Ser Leu Gly Leu Val Thr Gly Gly Asp Val Asn Ser Arg
                85                  90                  95

Ala Gln Glu Trp Lys Gln Ala His Leu Asn Thr Pro His Gly His Pro
            100                 105                 110

Ile Leu Leu Ala His Ala Leu Cys Pro Pro Ala Ile Asp Pro Lys His
        115                 120                 125

Lys His Glu Pro Gln Arg Ser Pro Ile Lys Val Val Ala Ala Met Ala
    130                 135                 140

<210> SEQ ID NO 5
<211> LENGTH: 6
<212> TYPE: DNA
<213> ORGANISM: Artificial
<220> FEATURE:
<223> OTHER INFORMATION: Synthesized Sequence

<400> SEQUENCE: 5 ccaggt                                                                 6

<210> SEQ ID NO 6
<211> LENGTH: 1745
<212> TYPE: DNA
<213> ORGANISM: Artificial
<220> FEATURE:
<223> OTHER INFORMATION: Synthesized Sequence

<400> SEQUENCE: 6
atgaatggca ttcacgatac tggcggagca catggttatg ggccggttta cagagaaccg     60
aacgaacccg tctttcgcta cgactgggaa aaaacggtca tgtccctgct cccggcgctg    120
ctcgccaacg gcaacttcaa cctcgatgaa tttcggcatt cgatcgagcg aatgggcccg    180
gcccactatc tggagggaac ctactacgaa cactggcttc atgtctttga gaacctgctg    240
gtcgagaagg gtgtgctcac ggccacggaa gtcgcgaccg gcaaggctgc gtctggcaag    300
```

| | |
|---|---|
| acggcgacgc cggtgctgac gccggccatc gtggacggac tgctcagcac cggggcttct | 360 |
| gccgcccggg aggagggtgc gcgggcgcgg ttcgctgtgg gggacaaggt tcgcgtcctc | 420 |
| aacaagaacc cggtgggcca tacccgcatg ccgcgctaca cgcggggcaa agtggggaca | 480 |
| gtggtcatcg accatggtgt gttcgtgacg ccggacaccg cggcacacgg aaagggcgag | 540 |
| caccccagc acgtttacac cgtgagtttc acgtcggtcg aactgtgggg gcaagacgct | 600 |
| tcctcgccga aggacacgat tcgcgtcgac ttgtgggatg actacctgga gccagcgcca | 660 |
| ggtgggcaat cacacacgca tgaccaccat cacgacgggt accaggcacc gcccgaagac | 720 |
| atcgcgctgc gggtcaaggc cttggagtct ctgctgatcg agaaaggtct tgtcgaccca | 780 |
| gcggccatgg acttggtcgt ccaaacgtat gaacacaagg taggcccccg aaacggcgcc | 840 |
| aaagtcgtgg ccaaggcctg ggtggaccct gcctacaagg cccgtctgct ggcagacggc | 900 |
| actgccggca ttgccgagct gggcttctcc ggggtacagg gcgaggacat ggtcattctg | 960 |
| gaaaacaccc ccgccgtcca caacgtcttc gtttgcacct tgtgctcttg ctacccatgg | 1020 |
| ccgacgctgg gcttgccccc tgcctggtac aaggccgcgc cctaccggtc cgcatggtg | 1080 |
| agcgaccccgc gtggggttct cgcggagttc ggcctggtga tccccgccaa caaggaaatc | 1140 |
| cgcgtctggg acaccacggc cgaattgcgc tacatggtgc tgccggaacg gcccgcggga | 1200 |
| actgaagcct acagcgaaga acaactggcc gaactcgtta cccgcgattc gatgatcggc | 1260 |
| accggcctgc ccacccaacc caccccatct cattgaaagg agatatagat atgaaagacg | 1320 |
| aacggtttcc attgccagag ggttcgctga aggacctcga tggccctgtg tttgacgagc | 1380 |
| cttggcagtc ccaggcgttt gccttggtgg tcagcatgca caaggccggt ctctttcagt | 1440 |
| ggaaagactg ggccgagacc ttcaccgccg aaatcgacgc ttccccggct ctgcccggcg | 1500 |
| aaagcgtcaa cgacacctac taccggcaat gggtgtcggc gctggaaaag ttggtggcgt | 1560 |
| cgctggggct tgtgacgggt ggagacgtca actcgcgcgc acaggagtgg aaacaggccc | 1620 |
| acctcaacac cccacatggg cacccgatcc tgctggccca tgcgctttgc ccgccagcga | 1680 |
| tcgaccccaa gcacaagcac gagccacaac gctcaccgat caaggtcgtt gccgcaatgg | 1740 |
| cttga | 1745 |

<210> SEQ ID NO 7
<211> LENGTH: 1782
<212> TYPE: DNA
<213> ORGANISM: Artificial
<220> FEATURE:
<223> OTHER INFORMATION: Synthesized Sequence

<400> SEQUENCE: 7

| | |
|---|---|
| atgaatggca ttcacgatac tggcggagca catggttatg ggccggttta cagagaaccg | 60 |
| aacgaacccg tctttcgcta cgactgggaa aaaacggtca tgtccctgct cccggcgctg | 120 |
| ctcgccaacg gcaacttcaa cctcgatgaa tttcggcatt cgatcgagcg aatgggcccg | 180 |
| gcccactatc tggagggaac ctactacgaa cactggcttc atgtctttga gaacctgctg | 240 |
| gtcgagaagg gtgtgctcac ggccacggaa gtcgcgaccg caaggctgc gtctggcaag | 300 |
| acggcgacgc cggtgctgac gccggccatc gtggacggac tgctcagcac cggggcttct | 360 |
| gccgcccggg aggagggtgc gcgggcgcgg ttcgctgtgg gggacaaggt tcgcgtcctc | 420 |
| aacaagaacc cggtgggcca tacccgcatg ccgcgctaca cgcggggcaa agtggggaca | 480 |
| gtggtcatcg accatggtgt gttcgtgacg ccggacaccg cggcacacgg aaagggcgag | 540 |
| caccccagc acgtttacac cgtgagtttc acgtcggtcg aactgtgggg gcaagacgct | 600 |

```
tcctcgccga aggacacgat tcgcgtcgac ttgtgggatg actacctgga gccagcgcca    660
ggtgggcaat cacacacgca tgaccaccat cacgacgggt accaggcacc gcccgaagac    720
atcgcgctgc gggtcaaggc cttggagtct ctgctgatcg agaaaggtct tgtcgaccca    780
gcggccatgg acttggtcgt ccaaacgtat gaacacaagg taggccccg aaacggcgcc     840 aaagtcgtgg ccaaggcctg ggtggaccct gcctacaagg cccgtctgct ggcagacggc    900
actgccggca ttgccgagct gggcttctcc ggggtacagg gcgaggacat ggtcattctg    960
gaaaacaccc ccgccgtcca acgtcttc gtttgcacct tgtgctcttg ctacccatgg     1020
ccgacgctgg gcttgccccc tgcctggtac aaggccgcgc cctaccggtc cgcatggtg     1080 agcgacccgc gtgggttct cgcggagttc ggcctggtga tccccgccaa caaggaaatc    1140
cgcgtctggg acaccacggc cgaattgcgc tacatggtgc tgccggaacg gcccgcggga    1200
actgaagcct acagcgaaga caactggcc gaactcgtta cccgcgattc gatgatcggc     1260
accgccctgc ccacccaacc caccccatct catccaaatg gagatataga tatgcccacc    1320
ccatctcatc caaatggaga tatagatatg aaagacgaac ggtttccatt gccagagggt    1380
tcgctgaagg acctcgatgg ccctgtgttt gacgagcctt ggcagtccca ggcgtttgcc    1440
ttggtggtca gcatgcacaa ggccggtctc tttcagtgga aagactgggc cgagaccttc    1500
accgccgaaa tcgacgcttc cccggctctg cccggcgaaa cgtcaacga cacctactac     1560 cggcaatggg tgtcggcgct ggaaaagttg gtggcgtcgc tggggcttgt gacgggtgga    1620
gacgtcaact cgcgcgcaca ggagtggaaa caggcccacc tcaacacccc acatgggcac    1680
ccgatcctgc tggcccatgc gctttgcccg ccagcgatcg accccaagca caagcacgag    1740
ccacaacgct caccgatcaa ggtcgttgcc gcaatggctt ga                      1782

<210> SEQ ID NO 8
<211> LENGTH: 31
<212> TYPE: DNA
<213> ORGANISM: Artificial
<220> FEATURE:
<223> OTHER INFORMATION: DNA Primer

<400> SEQUENCE: 8
ggaattccat atgaatggca ttcacgatac t                                   31

<210> SEQ ID NO 9
<211> LENGTH: 38
<212> TYPE: DNA
<213> ORGANISM: Artificial
<220> FEATURE:
<223> OTHER INFORMATION: DNA Primer

<400> SEQUENCE: 9
catatctata tctcctttca cgctggctcc aggtagtc                            38

<210> SEQ ID NO 10
<211> LENGTH: 36
<212> TYPE: DNA
<213> ORGANISM: Artificial
<220> FEATURE:
<223> OTHER INFORMATION: DNA Primer

<400> SEQUENCE: 10
tgaaaggaga tatagatatg ggcaatcac acacgc                               36

<210> SEQ ID NO 11
```

```
<211> LENGTH: 37
<212> TYPE: DNA
<213> ORGANISM: Artificial
<220> FEATURE:
<223> OTHER INFORMATION: DNA Primer

<400> SEQUENCE: 11
catatctata tctcctttta atgagatggg gtgggtt                              37

<210> SEQ ID NO 12
<211> LENGTH: 36
<212> TYPE: DNA
<213> ORGANISM: Artificial
<220> FEATURE:
<223> OTHER INFORMATION: DNA Primer

<400> SEQUENCE: 12
taaaaggaga tatagatatg aaagacgaac ggtttc                               36

<210> SEQ ID NO 13
<211> LENGTH: 29
<212> TYPE: DNA
<213> ORGANISM: Artificial
<220> FEATURE:
<223> OTHER INFORMATION: DNA Primer

<400> SEQUENCE: 13
ccggaattct caagccattg cggcaacga                                       29

<210> SEQ ID NO 14
<211> LENGTH: 30
<212> TYPE: DNA
<213> ORGANISM: Artificial
<220> FEATURE:
<223> OTHER INFORMATION: DNA Primer

<400> SEQUENCE: 14
ggaattccat atgaatggca ttcacgatac                                      30

<210> SEQ ID NO 15
<211> LENGTH: 30
<212> TYPE: DNA
<213> ORGANISM: Artificial
<220> FEATURE:
<223> OTHER INFORMATION: DNA Primer

<400> SEQUENCE: 15
gcccaagctt tcaagccatt gcggcaacga                                      30

<210> SEQ ID NO 16
<211> LENGTH: 30
<212> TYPE: DNA
<213> ORGANISM: Artificial
<220> FEATURE:
<223> OTHER INFORMATION: DNA Primer

<400> SEQUENCE: 16
gcccaagctt tcaatgagat ggggtgggtt                                      30

<210> SEQ ID NO 17
<211> LENGTH: 39
<212> TYPE: DNA
<213> ORGANISM: Artificial
<220> FEATURE:
<223> OTHER INFORMATION: DNA Primer

<400> SEQUENCE: 17
```

-continued

```
tacctggagc cagcgccagg tgggcaatca cacacgcat                              39

<210> SEQ ID NO 18
<211> LENGTH: 39
<212> TYPE: DNA
<213> ORGANISM: Artificial
<220> FEATURE:
<223> OTHER INFORMATION: DNA Primer

<400> SEQUENCE: 18
cgtgtgtgat tgcccacctg gcgctggctc caggtagtc                              39

<210> SEQ ID NO 19
<211> LENGTH: 36
<212> TYPE: DNA
<213> ORGANISM: Artificial
<220> FEATURE:
<223> OTHER INFORMATION: DNA Primer

<400> SEQUENCE: 19
cccaccccat ctcatccaaa tggagatata gatatg                                 36

<210> SEQ ID NO 20
<211> LENGTH: 36
<212> TYPE: DNA
<213> ORGANISM: Artificial
<220> FEATURE:
<223> OTHER INFORMATION: DNA Primer

<400> SEQUENCE: 20
catatctata tctccatttg gatgagatgg ggtggg                                 36
```

FUSED NHASE WITH IMPROVED SPECIFIC ACTIVITY AND STABILITY

CROSS-REFERENCES AND RELATED APPLICATIONS

This application claims the benefit of priority to Chinese Application No. 201510226690.7, filed May 6, 2015, which is a divisional of Chinese Application No. 201510195795.0, entitled "A fused NHase with improved specific activity and stability", filed Apr. 22, 2015, which is herein incorporated by reference in its entirety.

BACKGROUND OF THE INVENTION

Field of the Invention

The present invention relates to the field of genetic engineering, and more particularly relates to a fused NHase with improved specific activity and stability.

Description of the Related Art

Nitrile hydratase (NHase; EC 4.2.1.84) is an enzyme catalyzing the hydration of a broad scope of nitriles to the corresponding amides. The NHase comprises a β-subunit, a α-subunit and a regulatory subunit and it is generally divided into the cobalt-type (Co-NHase) or the iron type (Fe-NHase) depending on the metal ion chelated with the active site.

NHase has been widely used in the industrial production of highly purified acrylamide and nicotinamide, since biotechnology synthesis has advantages of low-cost, low-energy consumption and less pollution compared to traditional chemical synthesis. However, most NHases with high activity are unstable during industrial application. For example, the NHases of *Pseudomonas chlororaphils* B23 and *Rhodococcus* sp. N-774 are unstable above 20° C., and the NHase of *Rhodococcus rhodochrous* J1 is merely stable between 10° C. and 30° C. In addition, it is necessary to maintain low reaction temperature to stabilize the NHases by refrigeration because of the exothermic reaction of nitrile-hydration, which usually causes enormous redundant energy cost. Furthermore, tolerance of NHase to high concentrations of the product is necessary in industrial manufacturing. Therefore, a more stable NHase with high activity and high tolerance is required for industrial manufacturing.

DETAILED DESCRIPTION

To solve the problems described above, the present invention provides a method of improving the specific activity, stability and tolerance of NHase. Usually, the subunits of NHase are separated, and they would be depolymerized at high temperatures which could result in enzyme inactivation. Therefore, the present invention fuses the β- and α-subunits with covalent bonds through molecular approaches, which eliminates the possibility of subunits depolymerization. The resulted fused NHase with improved stability is more suitable for using in the industrial production of acrylamide and the fusion strategy could be applicable for different NHases with separated subunits.

The present invention provides a mutant NHase with improved specific activity and stability. The β- and α-subunits of the mutant NHase are fused in the mutant NHase, and the regulatory subunit is either fused or coexpressed with the fused α- and β-subunits.

In one embodiment of the present invention, the nucleotide sequence of the mutant NHase from 5' to 3' is β-subunit gene (B gene), α-subunit gene (A gene), and regulatory subunit gene (P14K gene) fused together.

In one embodiment of the present invention, the mutant NHase is reconstructed from the parent NHase whose nucleotide sequence is SEQ ID NO: 1. And the amino acid sequences of the α-subunit, β-subunit and regulatory subunit of the mutant NHase are the same as those of the parent NHase from *Pseudomonas putida* NRRL-18668.

In one embodiment of the present invention, the amino acid sequences which encode the β-subunit, α-subunit and regulatory subunit are SEQ ID NO: 2, SEQ ID NO: 3 and SEQ ID NO: 4, respectively.

The B gene and A gene are linked by a linker, and the nucleotide sequence of the linker is SEQ ID NO: 5.

In one embodiment of the present invention, the nucleotide sequence of the mutant NHase is SEQ ID NO.6 or SEQ ID NO.7.

The present invention also provides plasmids containing the amino acid sequences of the mutant NHase above and genetically engineered strains expressing the mutant NHase.

In one embodiment of the present invention, the genetically engineered strain is a recombinant *E. coli* BL21 (DE3).

The present invention also provides a method of constructing a genetically engineered strain expressing the mutant NHase.

In one embodiment of the present invention, the method of constructing the genetically engineered strain comprises cloning the nucleotide sequence shown in SEQ ID NO: 6 or SEQ ID NO: 7 to the expression plasmid of pET-28a to make a recombinant plasmid and transforming the recombinant plasmid into *E. coli* BL21(DE3).

The present invention also provides a method of producing NHases by the genetically engineered strain. The recombinant *E. coli* expressing the mutant NHase was cultivated in 2YT medium (tryptone 16 g/L, yeast extract 10 g/L, NaCl 5 g/L) at 37° C. When the optical density at 600 nm ($OD_{600}$) of the culture reached 0.8, isopropyl-D-1-thiogalactoside (IPTG) and $CoCl_2.6H_2O$ were added to the medium to induce the expression and maturization of NHase. The culture was subsequently incubated at 24° C. for 16 h.

The present invention also provides a method of improving the specific activity and stability of NHase, wherein the NHase is made by fusing the B and A gene together and coexpress the P14K gene, or by fusing the B, A and P14K gene together.

In one embodiment, the present invention provides a method is to fuse the B, A and P14K gene from 5' to 3' in the order of "B gene, A gene, P14K gene", and the B and A gene are connected by a linker whose nucleotide sequence is set forth in SEQ ID NO: 5.

The application of the mutant NHase, especially the application of the mutant NHase in acrylamide production is also under the scope of the present invention.

The mutant NHases obtained by the gene fusion strategy of the present invention exhibited significantly improved specific activity, thermostability and product tolerance than those of the wild type NHase.

EXAMPLES

Materials and Methods:

2YT medium: 16 g·L$^{-1}$ tryptone, 10 g·L$^{-1}$ yeast extract, 5 g·L$^{-1}$ NaCl.

The activity of NHase was detected by the method described as follows. The reaction mixture contained 500 μL 200 mM 3-cyanopyridine and 10 μl of the appropriate amount of the enzyme solution. The reaction was performed at 25° C. for 10 min and terminated with the addition of 500 μL of acetonitrile. Then the supernatant was collected by centrifugation and filtered though a 0.22 μm pore-size filter before measured by HPLC. One unit (U) of NHase activity is defined as the amount of enzyme that released 1 μmol nicotinamide per min under these assay conditions.

HPLC conditions: the mobile phase was water-acetonitrile buffer; detection wavelength was 215 nm; the column was C18 column.

Example 1: Construction of the Recombinant *E. coli* Expressing the Wild Type NHases-BAP14K Construction of the recombinant *E. coli* expressing the wild type NHases-BAP14K was carried out by the following steps:

(1) Amplification of the parent NHase gene: Primers were designed according to the published sequence in NCBI to amplify the ABP14K gene encoding the parent NHase from *P. Putida*. The amino acid sequence of the β-subunit, α-subunit and regulatory subunit of the parent NHases were SEQ ID NO: 2, SEQ ID NO: 3 and SEQ ID NO: 4, respectively.

(2) Construction of recombinant plasmid containing the ABP14K gene: the amplified DNA fragment of step 1 was digested with Nde I and Hind III, and then ligated into the Nde I and Hind III sites of pET-24a to create a recombinant plasmid containing the ABP14K gene. The recombinant plasmid was named pET-24a-ABP14K.

(3) Construction of recombinant plasmid containing the full-length BAP14K gene: pET-24a-ABP14K was used as a template. B gene was amplified by primer pairs B-up (SEQ ID NO: 8) and B-down(BA) (SEQ ID NO: 9), A gene was amplified by primer pairs A-up(BA) (SEQ ID NO: 10) and A-down(AP) (SEQ ID NO: 11), and the P14K gene was amplified by primer pairs P14K-up(AP) (SEQ ID NO: 12) and P-down (SEQ ID NO: 13). The same amount of B, A, P gene were used as templates and the full-length BAP14K gene was amplified by an overlap extension PCR protocol with primer pairs B-up (SEQ ID NO: 8) and P-down (SEQ ID NO: 13). The recombinant plasmid containing the BAP14K gene was named pET-24a-BAP14K, and the NHase expressed by pET-24a-BAP14K was defined as the wild type NHase.

Transformation of pET-24a-BAP14K into *E. coli* BL21 (DE3): The recombinant plasmid pET-24a-BAP14K was transformed into *E. coli* BL21 (DE3). The positive transformants expressing the wild type NHase were screened.

Primers used in the present invention were shown in Tab. 1.

TABLE 1

Primers

| Primer | sequence (5' to 3') | SEQ ID NO |
|---|---|---|
| B-up | GGAATTC*CATATG*AATGGCATTCACGATACT | 8 |
| B-down (BA) | CATATCTATATCTCCTTTCACGCTGGCTCCAGGTAGTC | 9 |
| A-up(BA) | TGAAAGGAGATATAGATATGGGGCAATCACACACGC | 10 |
| A-down (AP) | CATATCTATATCTCCTTTTAATGAGATGGGGTGGGTT | 11 |
| P14K-up (AP) | TAAAAGGAGATATAGATATGAAAGACGAACGGTTTC | 12 |
| P-down | CCG*GAATTC*TCAAGCCATTGCGGCAACGA | 13 |
| B-NdeI-up | GGAATTC*CATATG*AATGGCATTCACGATAC | 14 |
| P-HindIII-down | GCCC*AAGCTT*TCAAGCCATTGCGGCAACGA | 15 |
| A-HindIII-down | GCCC*AAGCTT*TCAATGAGATGGGGTGGGTT | 16 |
| Linker1-up | <u>TACCTGGAGCCAGCGC</u>CAGGT<u>GGGCAATCACACACGCAT</u> | 17 |
| Linker1-down | <u>CGTGTGTGATTGCCC</u>ACCTG<u>GCGCTGGCTCCAGGTAGTC</u> | 18 |
| Linker2-up | <u>CCCACCCCATCTCATCCAAAT</u>GGAGATATAGATATG | 19 |
| Linker2-down | <u>CATATCTATATCTCCATTTGG</u>ATGAGATGGGGTGGG | 20 |

Note:
restriction sites were in italics and bold; overlapping sequences were underlined.

Example 2: Construction of the Recombinant *E. coli* Expressing the NHase-(BA)P14K The recombinant *E. coli* expressing the NHase-(BA)P14K was constructed by the following steps:

(1) The B and A gene were fused by linker 1 (SEQ ID NO: 5) by primer pairs Linker1-up (SEQ ID NO: 17) and Linker1-down (SEQ ID NO: 18) using pET-24a-BAP14K as a template. The resulted pET-24a-(BA)P14K was used as a template to amplify the (BA)P14K gene by primer pairs B-Nde I-up (SEQ ID NO: 14) and P-Hind III-down (SEQ ID NO: 15). The amplified (BA)P14K fragment was then digested with Nde I and Hind III, ligated into the Nde I and Hind III sites of pET-28a. The resulted recombinant plasmid pET-28a-(BA)P14K could express a fused NHase (nucleotide sequence shown in SEQ ID NO: 6), whose β- and α-subunits were fused together and the regulatory subunit was coexpressed. The NHase expressed by pET-28a-(BA) P14K was defined as NHase-(BA)P14K.

(2) The recombinant plasmid pET-28a-(BA)P14K was transformed into *E. coli* BL21 (DE3). Positive transformants expressing the NHase-(BA)P14K were screened.

Example 3: Construction of the Recombinant *E. coli* Expressing the NHase-(BAP14K)

The recombinant *E. coli* expressing the NHase-(BAP14K) was constructed by the following steps:

Primer pairs Linker2-up (SEQ ID NO: 19) and Linker2-down (SEQ ID NO: 20) were used to connect the A gene and P14K gene and pET-28a-(BA)P14K was the template. The resulted plasmid pET-28a-(BAP14K) contained a fused NHase gene whose B, A, and P14K gene fragments were fused together (nucleotide sequence shown in SEQ ID NO: 7). The NHase expressed by pET-28a-(BAP14K) was defined as NHase-(BAP14K).

The recombinant plasmid pET-28a-(BAP14K) was transformed into *E. coli* BL21 (DE3). The positive transformants expressing the NHase-(BAP14K) were screened.

Example 4: Expression and Characterization of the NHases

The *E. coli* recombinants obtained in example 1-3 were used to express the NHases.

The *E. coli* recombinants were firstly cultivated in 10 ml of liquid 2YT medium containing 50 μg/ml kanamycin at 37° C., then transferred to 500 ml of liquid 2YT medium with 1% inoculation. When $OD_{600}$ of the culture reached 0.8, IPTG was added to a final concentration of 0.4 mM to induce NHase expression, and $CoCl_2 \cdot 6H_2O$ was added to a final concentration of 0.05 g/l to obtain mature NHase. The culture was subsequently incubated at 24° C. for 16 h and then the cells were harvested for SDS-PAGE.

Figure 1:
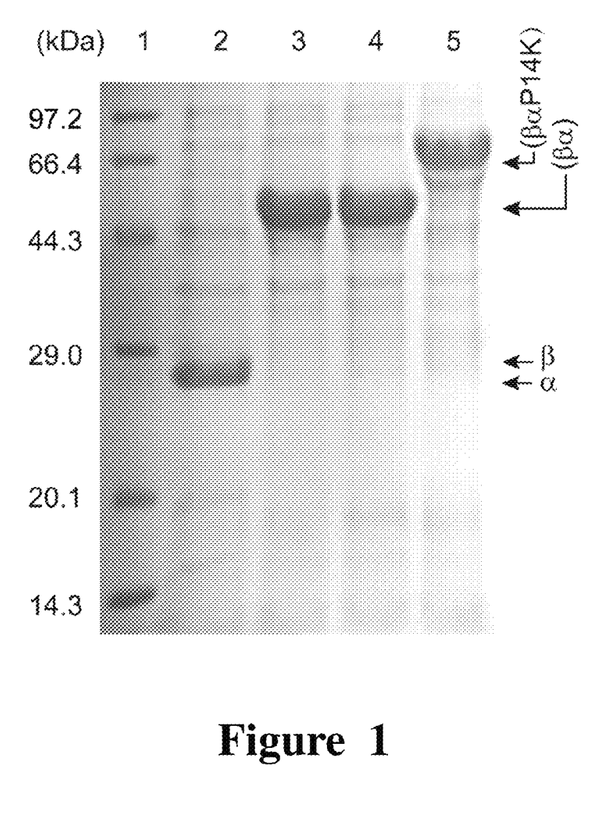
FIG. 1. SDS-PAGE of the wild type NHases and the fused NHases expressed by *E. coli*. Line 1, molecular weight marker; line 2, the wild type NHases; line 3, the mutant NHase-(BA); line 4, the mutant NHase-(BA)P14K; line 5, the mutant NHase-(BAP14K).

Results indicated that the wild type NHase, NHase-(BA)P14K and NHase-(BAP14K) were successfully expressed, as shown in FIG. 1. The line 3 represented the mutant NHase-(BA) whose β-subunit and α-subunit were just fused in the absence of the regulatory subunit.

The characteristics of the subunits fused NHases:

Specific Activity

Determination of NHases was conducted by the following method. The *E. coli* recombinants were collected by centrifugation and resuspended with a 0.01M phosphate buffer (pH 7.5) twice before ultrasonic disruption. The enzyme in the supernatant was purified and then the enzyme activity was detected by HPLC.

Compared with 324.8 U/mg of the wild type NHase, the specific activity of NHase-(BA)P14K and NHase-(BAP14K) were 499.2 U/mg and 452.5 U/mg, which were increased by 53.7% and 39.3%, respectively. In addition, the specific activity of NHase-(BA) (FIG. 1, line 3) was 69.1 U/mg, indicating that the P14K was also necessary for cobalt incorporation in the fused NHase.

Furthermore, the kinetic parameters ($K_m$, $V_{max}$, $k_{cat}$ and $k_{cat}/K_m$) of NHase-(BA)P14K and NHase-(BAP14K) were compared with the wild-type NHase. Results showed that the $k_{cat}$ value of NHase-(BA)P14K (723.4 $s^{-1}$) and NHase-(BAP14K) (676.5 $s^{-1}$) were both approximately 2-fold of the wild-type NHase (335.1 $s^{-1}$), indicating that the fused NHases exhibited faster catalyze rate. In addition, the $k_{cat}/K_m$ value of NHase-(BA)P14K ($11.8 \cdot 10^3$ $s^{-1}M^{-1}$) was about 1.5 fold of the wild-type NHase ($8.1 \cdot 10^3$ $s^{-1}M^{-1}$), indicating higher catalytic efficiency of NHase-(BA)P14K.

Thermostability

The thermostability of the NHases was measured by the following steps. First, the eppendorf tube containing the enzyme solution was placed in a metal bath at 50° C. for a while before placed on ice. And then, the tube was placed at 25° C. in the metal bath and 200 mM 3-cyanopyridine (substrate) was added to it. Ten minutes later, acetonitrile was added to terminate the reaction.

Figure 2:
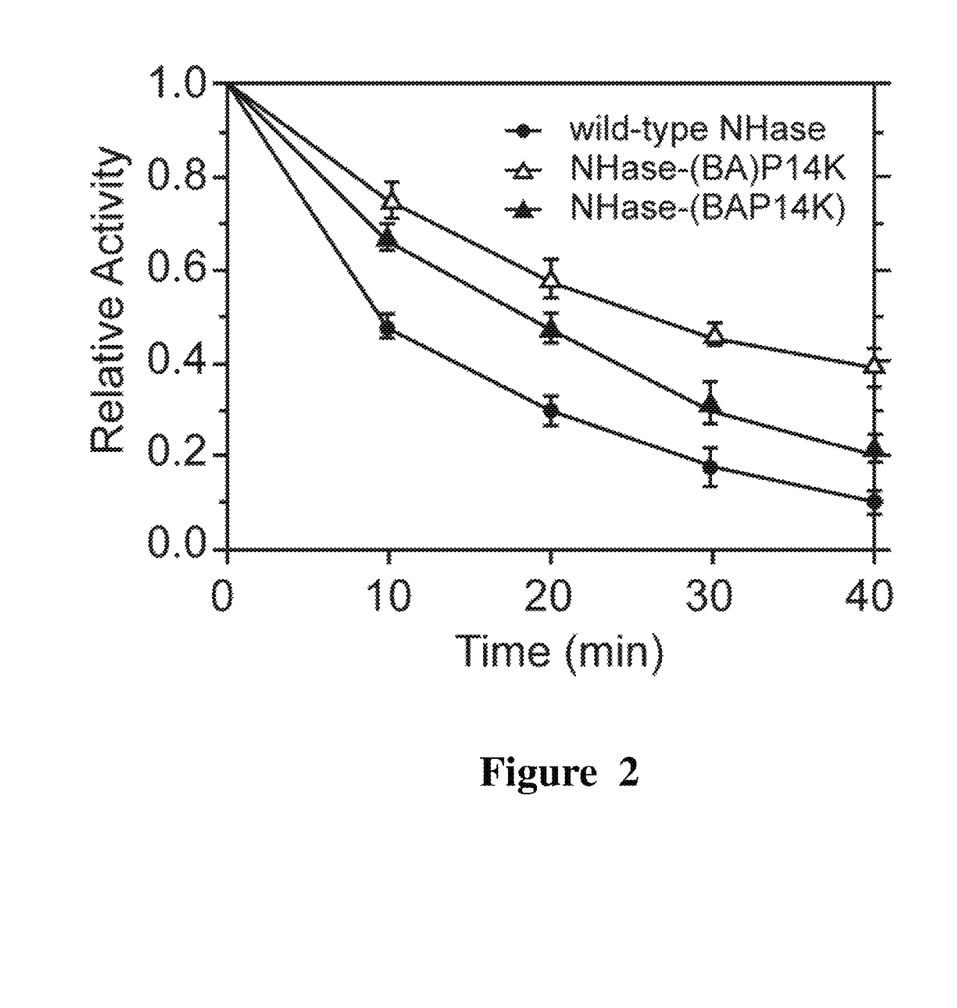
FIG. 2. Half-time in 50° C. of the wild type NHase and the fused NHases.

As shown in FIG. 2, the half-life times of NHase-(BA)P14K and NHase-(BAP14K) were 26 min and 18 min, respectively, while that of the wild-type NHase was 9 min. Results suggested that the NHase-(BA)P14K and NHase-(BAP14K) exhibited higher thermostability than the wild-type NHase.

Product Tolerance of the NHases

Figure 3:
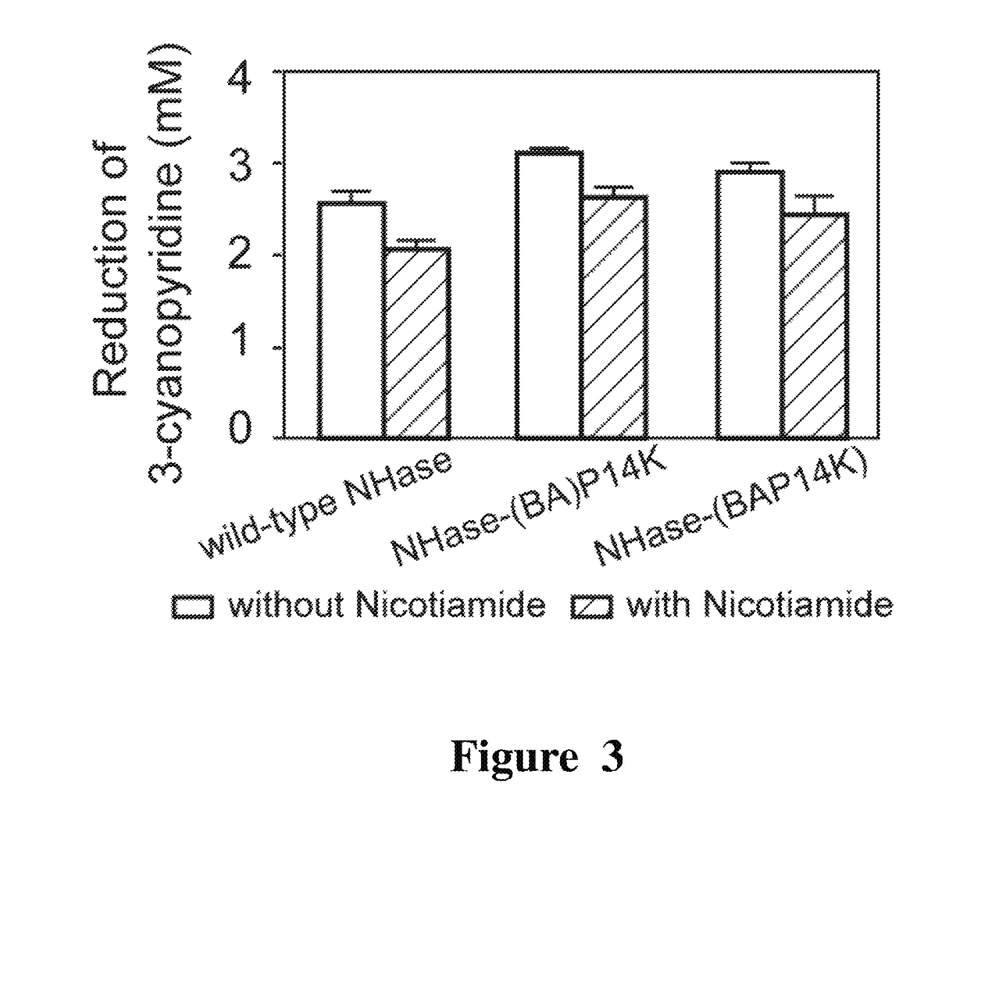
FIG. 3. Product tolerance of the wild type NHase and the fused NHases.

The product tolerance of the NHases was measured by the following method. The reaction was conducted in 20 mM 3-cyanopyridine (substrate) with and without 0.5 M nicotinamide (product) for 10 min. The reduction of 3-cyanopyridine in each reaction was measured (FIG. 3), and the reduction ratio (the proportion of the reduced 3-cyanopyridine amount in the reaction with and without 0.5 M nicotinamide) was calculated.

Results showed that the consumption of substrate of NHase-(BA)P14K and NHase-(BAP14K) in product containing reaction systems were increased by 26% and 18%, respectively compared with the wild type NHase, and increased by 23% and 15% respectively in reaction systems without product. In addition, the reduction ratios of NHase-(BA)P14K (0.86) and NHase-(BAP14K) (0.83) were higher than that of the wild type (0.80), indicating that the fused NHases exhibited stronger product tolerance than that of the wild type.

The Optimum pH

Figure 4:
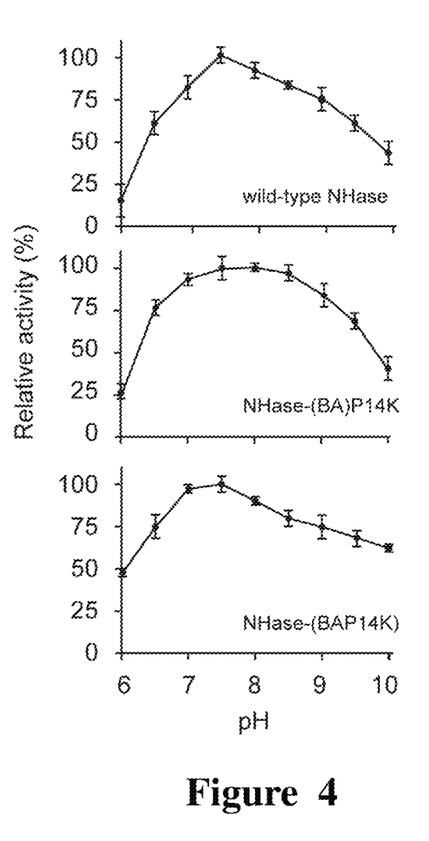
FIG. 4. The optimal pH of the wild type NHase and the fused NHases.

The enzyme activities of the fused NHases were measured under different pH and compared with the wild type, and the activity under their respective optimum pH was defined as 1(100%). As shown in FIG. 4, the optimum pH of the three NHases were about 7.5.

These data showed that the specific activity, thermostability and product tolerance of NHase could be significantly increased by fusing the β subunit and the α subunit with the regulatory subunit fused or coexpressed at the same time.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A mutant Nitrile hydratase (NHase) comprising a fusion protein having from N-terminus to C-terminus the following NHase subunits and protein: β-subunit, α-subunit and activator protein, wherein said fusion protein has improved specific activity and stability compared to an NHase having the same subunits not together as a fusion protein.

2. The mutant NHase of claim 1, wherein said β-subunit and said α-subunit are linked by a linker, wherein the nucleotide sequence encoding said linker is set forth in SEQ ID NO: 5.

3. The mutant NHase of claim 1, wherein the amino acid sequence of said β-subunit, said α-subunit and said activator protein are set forth in SEQ ID NO: 2, SEQ ID NO: 3 and SEQ ID NO: 4, respectively.

4. The mutant NHase of claim 1, wherein the nucleotide sequence encoding said mutant NHase is set forth in SEQ ID NO: 7.

5. The mutant NHase of claim 1, wherein said mutant NHase is expressed by a plasmid.

6. The mutant NHase of claim 1, wherein said mutant NHase is expressed by a genetically engineered strain.

7. The mutant-NHase of claim 6, wherein said genetically engineered strain is Escherichia coli.

8. The mutant NHase of claim 6, wherein said genetically engineered strain is constructed by the following steps:
   a), cloning the nucleotide sequence shown in SEQ ID NO: 7 to the expression vector of pET-28a to create a recombinant plasmid; and
   b), transforming the recombinant plasmid into E. coli BL21.

9. A method of improving the specific activity and stability of a NHase, comprising fusing from the N-terminus to the C-terminus the following NHase subunits and protein: β-subunit, α-subunit and activator protein.

10. A method of producing acrylamide, comprising contacting the mutant NHase of claim 1 with a substrate to make acrylamide.

* * * * *